(12) United States Patent
Bromberg et al.

(10) Patent No.: US 7,273,891 B1
(45) Date of Patent: Sep. 25, 2007

(54) STABLE COPOLYMERS

(75) Inventors: Lev Bromberg, Swampscott, MA (US); Elmer C. Lupton, Charlestown, MA (US)

(73) Assignee: B L Partnership, Charlestown, MA (US)

( * ) Notice: Subject to any disclaimer, the term of this patent is extended or adjusted under 35 U.S.C. 154(b) by 669 days.

(21) Appl. No.: 10/342,924

(22) Filed: Jan. 15, 2003

Related U.S. Application Data

(60) Provisional application No. 60/349,819, filed on Jan. 17, 2002.

(51) Int. Cl.
*A61K 47/00* (2006.01)
(52) U.S. Cl. ............ 514/772.1; 514/772; 424/400
(58) Field of Classification Search ............ None
See application file for complete search history.

(56) References Cited

U.S. PATENT DOCUMENTS 5,939,485 A  8/1999  Bromberg et al.
6,316,011 B1  11/2001  Ron et al.
6,486,213 B1  11/2002  Chen et al.
7,008,628 B2 *  3/2006  Ron et al. .................. 424/401

FOREIGN PATENT DOCUMENTS

WO   WO95/24430   9/1995
WO   WO98/06438   2/1998
WO   WO98/50005   11/1998

OTHER PUBLICATIONS

L. Bromberg, Polyether modified Poly (acrylic acid): Synthesis and Applications, Ind. Eng. Chem. Res., 37,4267-4274, 1998, Am Chem Soc., Washington, D.C.

* cited by examiner

*Primary Examiner*—Michael P. Woodward
*Assistant Examiner*—Eric E. Silverman
(74) *Attorney, Agent, or Firm*—Elmer C. Lupton

(57) ABSTRACT

A graft reverse thermal hydrogel which does not show substantial loss of complex viscosity at and up to 20 degrees above the transition temperature upon autoclaving or aging. Other embodiments include the graft reverse thermal copolymer which can be dissolved in water to produce the graft reverse thermal hydrogel, a process for manufacturing the graft reverse thermal copolymer and hydrogel and applications for the stable graft reverse thermal hydrogel.

27 Claims, 2 Drawing Sheets

Rheological testing of "stabilized" 2 w/v% aqueous solution of Pluronic-PAA (pH 7.0) before autoclaving and after each consecutive cycle of autoclaving. Frequency of oscillatory shear 6.28 rad/s, strain 1.7%.

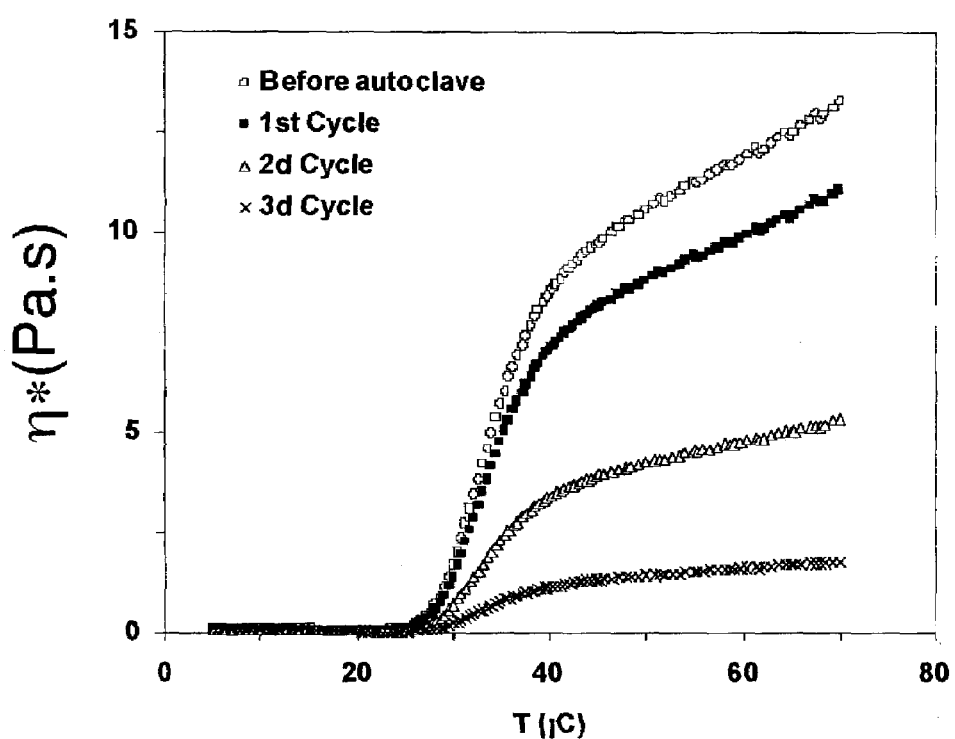
Fig.1. Rheological testing of "unstabilized" 2 w/v% aqueous solution of Pluronic-PAA (pH 7.0) before autoclaving and after each consecutive cycle of autoclaving. Frequency of oscillatory shear 6.28 rad/s, stress 60 mPa.

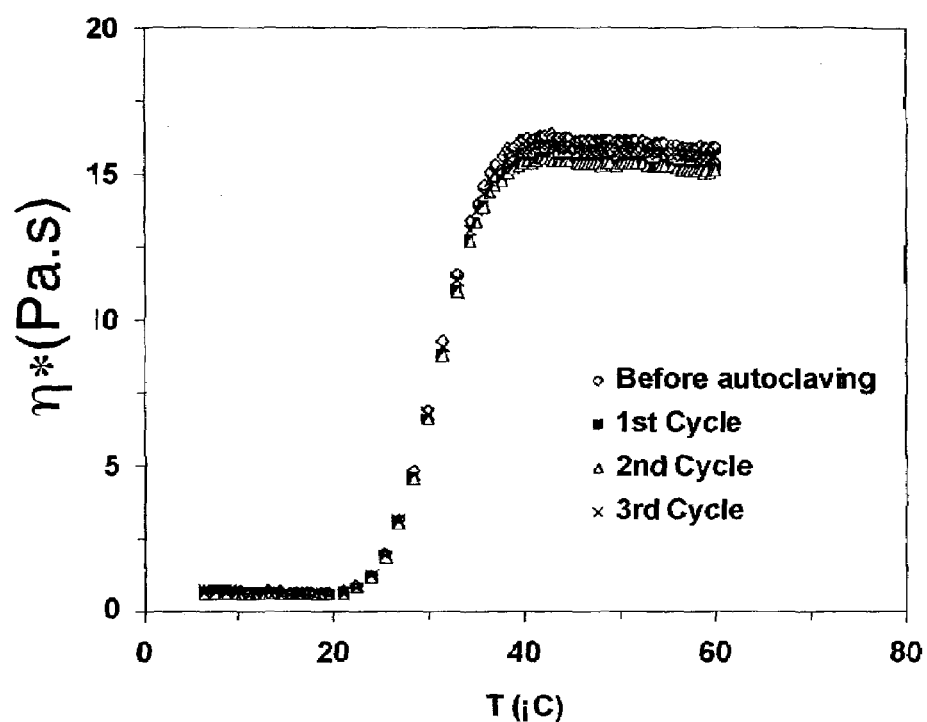
Fig.2. Rheological testing of "stabilized" 2 w/v% aqueous solution of Pluronic-PAA (pH 7.0) before autoclaving and after each consecutive cycle of autoclaving. Frequency of oscillatory shear 6.28 rad/s, strain 1.7%.

US 7,273,891 B1

STABLE COPOLYMERS

PRIORITY CLAIMED TO PROVISIONAL APPLICATION

This application claims the benefit of provisional patent application 60/349,819 filed Jan. 17, 2002 "Stable Copolymers", the contents of which are incorporated in their entirety herein by reference.

FIELD OF THE INVENTION

The present invention relates to graft reverse thermal copolymer solutions which show enhanced stability. The present invention further relates to water soluble graft reverse thermal copolymer solids which can be used to manufacture the graft reverse thermal copolymer solutions. The present invention further relates to the use of these graft reverse thermal copolymer solutions in medical and pharmaceutical applications and in other areas.

BACKGROUND OF THE INVENTION

All references mentioned throughout this document are explicitly incorporated included herein by reference.

Recently, a novel synthetic route toward hydrophobically modified poly(acrylic acid), which is a hybrid between post-polymerization modification and a free-radical copolymerization, has been discovered [Bromberg, L. A Novel Family of Thermogelling Materials via C—C Bonding Between Poly(acrylic acid) and Poly(ethylene oxide)-b-poly (propylene oxide)-b-poly(ethylene oxide), J. Phys. Chem. B 1998, 102, 1956; Bromberg, L. Polyether-modified Poly (acrylic acid): Synthesis and Properties, Ind. Eng. Chem. Res. 1998, 37, 4267]. These references are explicitly incorporated herein by reference. Without intending to be bound by any particular mechanism, it is believed that PAA segments are grafted onto a polyether backbone (typically represented by a PEO-PPO-PEO copolymer) via C—C bonding. It is believed that he PEO-PPO-PEO copolymers act as chain transfer agents in polymerization of acrylic acid, when hydrogen abstraction from these polyethers is allowed. The transfer to propagating polymer in acrylic emulsion polymerization is known to be often substantial and leading to a gelled polymer. The copolymers of PAA and polyethers resulting from the novel synthetic route possess micelle-forming capability and have been used in topical drug delivery, pharmaceuticals, and consumer products [Ron, E. S., Bromberg, L., Luszak, S., Kearney, M., Deaver, D. R., Schiller, M. Smart Hydrogel™: a Novel Mucosal Delivery System, Proc. Intern. Symp. Control. Release Bioact. Mater. 1997, 24, 407; Bromberg, L. E., Mendum, T. H. E., Orkisz, M. J., Ron, E. S., Lupton, E. S. Applications of Poly (oxyethylene-b-oxypropylene-b-oxyethylene)-g-poly (acrylic acid) Polymers (Smart Hydrogel™) in Drug Delivery, Proc. Polym. Mater. Sci. Eng. 1997, 76, 273; Orkisz, M. J., Bromberg, L., Pike, R., Lupton, E. C., Ron, E. S. Polyoxyethylene-b-polyoxypropylene-b-polyoxyethylene-g-poly(acrylic acid) Polymers (Smart Hydrogel™) as a Carrier in Controlled Delivery of Proteins and Peptides, Proc. Polym. Mater. Sci. Eng. 1997, 76, 276; Bromberg, L. E., Orkisz, M. J., Ron, E. S. Bioadhesive Properties of Polyoxyethylene-b-polyoxypropylene-b-polyoxyethylene-g-poly(acrylic acid) Polymers (Smart Hydrogel™), Polym. Prepr. 1997, 38, 626; Bromberg, L. E., Ron, E. S. Protein and Peptide Release from Temperature-Responsive Gels and Thermogelling Polymer Matrices, Adv. Drug Delivery Revs. 1998, 31, 197; Bromberg, L. Self-assembly in Aqueous Solutions of Polyether-modified Poly(acrylic acid), Langmuir 1998, 14, 5806; Bromberg, L. Scaling of Rheological Properties of Hydrogels from Associating Polymers, Macromolecules 1998, 31, 6148; Bromberg, L. Properties of Aqueous Solutions and Gels of Poly(ethylene oxide)-b-poly (propylene oxide)-b-poly(ethylene oxide)-g-poly(acrylic acid), J. Phys. Chem. B 1998, 102, 10736; Bromberg, L. E., Goldfeld, M. G. Self-assembly in Aqueous Solutions of Hydrophobically Modified Poly(acrylic acid), Polym. Prepr. 1998, 39, 681; Bromberg, L. Interactions between Hydrophobically Modified Polyelectrolytes and Mucin, Polym. Prepr. 1999, 40, 616; Huibers, P. D. T., Bromberg, L. E., Robinson, B. H., Hatton, T. A. Reversible Gelation in Semidilute Aqueous Solutions of Associative Polymers: a Small-angle Neutron Scattering Study, Macromolecules, 1999, 32, 4889; Bromberg, L. E., Barr, D. P. Aggregation Phenomena in Aqueous Solutions of Hydrophobically Modified Polyelectrolytes. A Probe Solubilization Study, Macromolecules 1999, 32, 3649; Bromberg, L., Salvati, L. Bioactive Surfaces via Immobilization of Self-assembling Polymers Onto Hydrophobic Materials, Bioconjugate Chem. 1999, 10, 678; Bromberg, L., Magner, E. Release of Hydrophobic Compounds From Micellar Solutions of Hydrophobically Modified Polyelectrolytes, Langmuir 1999, 15, 6792; Bromberg, L., Temchenko, M. Loading of Hydrophobic Compounds into Micellar Solutions of Hydrophobically Modified Polyelectrolytes, Langmuir 1999, 15, 8627; Bromberg, L., Temchenko, M., Colby, R. H. Interactions Among Hydrophobically Modified Polyelectrolytes and Surfactants of the Same Charge, Langmuir 2000, 16, 2609, etc.]. These references are explicitly incorporated herein by reference.

These materials are also described in patents and patent applications including L. E. Bromberg, E. C. Lupton, M. E. Schiller, M. J. Timm, G. McKinney, "Responsive Polymer Networks and Methods of their Use", U.S. Pat. No. 5,939, 485, Aug. 17, 1999; L. E. Bromberg, E. C. Lupton Jr., M. E. Schiller, M. J. Timm, G. W. McKinney III, M. Orkisz, B. Hand, "Responsive Polymer Networks and Methods of Their Use", PCT WO 97/00275, 1997; E. S. Ron, L. Bromberg and M. Temchenko, "End modified thermal responsive hydrogels, U.S. Pat. No. 6,316,011, Nov. 13, 2001; E. S. Ron, L. Bromberg and M. Temchenko," End modified thermal responsive hydrogels, WO00/07603, Aug. 4, 1999. These references are explicitly incorporated herein by reference.

Specifically noted are these sections from these references. In Bromberg, L. Properties of Aqueous Solutions and Gels of Poly(ethylene oxide)-b-poly(propylene oxide)-b-poly(ethylene oxide)-g-poly(acrylic acid), J. Phys. Chem. B.; 1998; 102(52); 10736-10744, p 10738, col 2, line 40 to p 10739 col 1, line 3, (attached), which is included in this specification by reference. "The lower a values measured for all Pluronic-PAA samples to be in the range 0.48<a<0.59 at 15 C, along with the lower intrinsic viscosity to an equivalent molecular weight PAA suggest that the Pluronic-PAA samples possess higher molecular weight per repeat unit. This observation may be interpreted as a regular short-chain branching in Pluronic-PAA and is consistent with the synthetic mechanism, which involves chain transfer." In Huibers, P. D. T.; Bromberg, L. E.; Robinson, B. H.; Hatton, T. A. Reversible Gelation in Semidilute Aqueous Solutions of Associative Polymers: A Small-Angle Neutron Scattering Study, Macromolecules; 1999; 32(15); 4889-4894, p 4889, col 1, lines 2-12, which was included in this specification by reference. "The polymer formed from grafting the branched polyelectrolyte poly(sodium acrylate) (PAA) to the surface-active triblock copolymer poly(ethylene oxide)-b-poly(propylene oxide)-b-poly(ethylene oxide) (PEO-PPO-PEO) represents a class of unique new materials that undergo reversible gelation in semidilute (1 wt % and below) aqueous solutions over a narrow temperature range. 1-11 The covalent grafting via C—C bonding results in high molecular weight (above 105 Da) PEO-PPO-PEO-g-PAA polymers with regular short-chain branching" and in Huibers et. al Macromolecules, ibid., p 4892, col 2, lines 44-48 "The thermally reversible character of the Pluronic-PAA system can be attributed to its chemical composition and unique block-graft arrangement, resulting in a material with novel physical properties." The chemical structure of the material is shown in FIG. 3 which is FIG. 5 of Huibers et. al Macromolecules, ibid., p 4893. As FIG. 3 shows, in the "block-graft" structure, the polyacrylic acid chains become bonded onto the polyoxyalkylene molecules, with a carbon from each bonded polyacrylic acid chain replacing a hydrogen on a PEO or PPO moiety. Some polyacrylic acid chains can be bonded to more than one polyoxyalkylene molecule. Note such a multiply bonded PAA-polyoxyalkylene molecule at the lower right of the left hand drawing of FIG. 3.

Previously, the synthesis of such polymers resulted in polymers that were somewhat unstable in conditions of repetitive heating-cooling cycles or under elevated temperature conditions. Unexpectedly, we have discovered that avoidance of the exposure of the polymers to air in the process of their synthesis followed by lyophilization yields usefully stable polymers.

SUMMARY OF THE INVENTION

In one aspect, the invention is solution of a graft reverse thermal hydrogel, which solution, when measured at a temperature $T_{transition}+\Delta T$ where $\Delta T$ is between 0 and 20 degrees C., displays a complex viscosity after autoclaving which is not degraded to a large extent from its complex viscosity prior to autoclaving. In another aspect, the invention is the solid graft reverse thermal copolymer which, when dissolved in aqueous solution, will display a complex viscosity after autoclaving, when measured at a temperature $T_{transition}+\Delta T$ where $\Delta T$ is between 0 and 20 degrees C., which is not degraded to a large extent from its complex viscosity prior to autoclaving. In another aspect, the invention is a solution of a graft reverse thermal hydrogel, which solution, when measured at a temperature $T_{transition}+\Delta T$ where $\Delta T$ is between 0 and 20 degrees C., displays a complex viscosity after aging for one year at 25 degrees C. which is not degraded to a large extent from its complex viscosity prior to aging. In another aspect, the invention is the use of the solution of a graft reverse thermal hydrogel, which retains its complex viscosity after autoclaving or aging, for medical or pharmaceutical applications or for cosmetic applications.

We define the term "graft reverse thermal copolymer" to mean the materials taught by U.S. Pat. Nos. 5,939,485, 6,316,011 and similar copolymers manufactured by grafting a polyionic component onto a thermally responsive component during the process of free radical synthesis of the polyionic component. We define the term "graft reverse thermal hydrogel" to mean the aqueous solution of a graft reverse thermal copolymer which displays the property of increasing substantially in complex viscosity upon a relatively small change in solution temperature. In order to meet our definition of graft reverse thermal copolymer and graft reverse thermal hydrogel, the hydrogel must display the property of increasing substantially in complex viscosity upon a relatively small change in solution temperature. However, as is discussed below, upon autoclaving or other time-temperature exposure, a graft reverse thermal hydrogel and/or graft reverse thermal copolymer may lose its ability to display a substantially increased complex viscosity upon a relatively small change in solution temperature. This material would still fit our definition of graft reverse thermal hydrogel and graft reverse thermal copolymer during the period of time that it displayed the property of substantially increasing its complex viscosity upon a relatively small change in solution temperature.

We define the term "a medical or pharmaceutical application" to mean an application where the material or materials are used to achieve or to attempt to achieve a medical or pharmaceutical objective including a veterinary, dental or botanical or other such plant health related objective. Such an application would include but not be limited to the medical or pharmaceutical applications taught in L. E. Bromberg, E. C. Lupton, M. E. Schiller, M. J. Timm, G. McKinney, "Responsive Polymer Networks and Methods of their Use", U.S. Pat. No. 5,939,485, Aug. 17, 1999; L. E. Bromberg, E. C. Lupton Jr., M. E. Schiller, M. J. Timm, G. W. McKinney III, M. Orkisz, B. Hand, "Responsive Polymer Networks and Methods of Their Use", PCT WO 97/00275, 1997; E. S. Ron, L. Bromberg and M. Temchenko, "End modified thermal responsive hydrogels, U.S. Pat. No. 6,316,011, Nov. 13, 2001; E. S. Ron, L. Bromberg and M. Temchenko," End modified thermal responsive hydrogels, WO00/07603, Aug. 4, 1999. These references are explicitly included herein by reference. It also includes the medical or pharmaceutical applications taught in M. E. Schiller, S. H. Gehrke, E. C. Lupton Jr., T. Tanaka and X. Yu, "Novel Polymer Gel Networks and Methods of Use", PCT WO 96/02276, 1996 (Schiller) which is explicitly incorporated herein by reference. Schiller teaches the use of a crosslinked gel to achieve the medical or pharmaceutical objective; one type of embodiment of our invention uses the materials taught here to achieve the medical or pharmaceutical objective outlined by Schiller We define the term "a cosmetic application" to mean an application where the material or materials are used to achieve or to attempt to achieve a cosmetic objective. Such a cosmetic application would include but not be limited to the cosmetic applications taught in L. E. Bromberg, E. C. Lupton, M. E. Schiller, M. J. Timm, G. McKinney, "Responsive Polymer Networks and Methods of their Use", U.S. Pat. No. 5,939,485, Aug. 17, 1999; L. E. Bromberg, E. C. Lupton Jr., M. E. Schiller, M. J. Timm, G. W. McKinney III, M. Orkisz, B. Hand, "Responsive Polymer Networks and Methods of Their Use", PCT WO 97/00275, 1997; E. S. Ron, L. Bromberg and M. Temchenko, "End modified thermal responsive hydrogels, U.S. Pat. No. 6,316,011, Nov. 13, 2001; E. S. Ron, L. Bromberg and M. Temchenko," End modified thermal responsive hydrogels, WO00/07603, Aug. 4, 1999. These references are explicitly included herein by reference. It also includes the cosmetic applications taught in M. E. Schiller, S. H. Gehrke, E. C. Lupton Jr., T. Tanaka and X. Yu, "Novel Polymer Gel Networks and Methods of Use", PCT WO 96/02276, 1996 (Schiller) which is explicitly incorporated herein by reference. Schiller teaches the use of a crosslinked gel to achieve the cosmetic objective; one type of embodiment of our invention uses the materials taught here to achieve the cosmetic objective outlined by Schiller

BRIEF DESCRIPTION OF THE DRAWINGS

The invention will be understood with reference to the drawings in which:

FIG. 1. is a series of viscosity temperature curves of a graft reverse thermal hydrogel before autoclaving and after one, two and three autoclave cycles. This material shows thermal degradation to a large extent.

FIG. 2 is a series of viscosity-temperature curves of a graft reverse thermal hydrogel before autoclaving and after one, two and three autoclave cycles. This is the material of the invention and does not show thermal degradation to a large extent.

DETAILED DESCRIPTION OF THE INVENTION

Without intending to be bound by any particular theory, herein, we consider possible chemical mechanisms causing instability of Pluronic-PAA copolymers. The synthesis of these copolymers involves the use of free-radical initiators that are capable of thermal degradation forming radicals that are, in turn, prone to hydrogen abstraction. The former process is necessary for initiation of the polymerization of the monomer, while the latter is needed for grafting of the growing oligomer radicals onto polyether radicals. Synthetic scheme of the Pluronic-PAA copolymers involves free-radical polymerization of acrylic acid (reaction 1 below) with the chain transfer to Pluronic (reactions 2-4) resulting in what is believed to be grafting of PAA chains onto Pluronic backbone [Bromberg, L. A Novel Family of Thermogelling Materials via C—C Bonding Between Poly (acrylic acid) and Poly(ethylene oxide)-b-poly(propylene oxide)-b-poly(ethylene oxide), J. Phys. Chem. B 1998, 102, 1956; Bromberg, L. Polyether-modified Poly(acrylic acid): Synthesis and Properties, Ind. Eng. Chem. Res. 1998, 37, 4267] These references are explicitly included herein by reference:

   (1)

   (2)

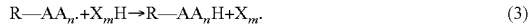   (3)

   (4)

where R. is the free radical, $X_mH$ is polyether, and AA is the acrylic acid monomer.

Efficiency of the grafting of PAA onto Pluronic backbone depends on grafting conditions, such as hydrogen abstraction power of the initiator, its concentration, etc. Optimized synthetic procedure results in about 90% of Pluronic initially present in the reaction mixture being chemically bound to PAA. Ammonium persulfate or peroxides such as lauroyl peroxide, benzoyl peroxide, etc. are often used in the synthesis of Pluronic-PAA, as they are capable of both initiation and hydrogen abstraction. As an example, we will consider effects of ammonium persulfate (APS):

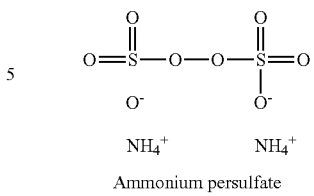

Ammonium persulfate

The peroxy —O—O— bond in APS is analogous to the one in organic peroxides. APS is a relatively strong oxidant ($E^O$=2.1 V). Ammonium persulfate dissolves in water to give the peroxydisulfate dianion. This compound decays to give the sulfate radical by either reductive (5) or homolytic (6) cleavage of the peroxy bond.

   (5)

   (6)

The sulfate radical then attacks the monomer (acrylic acid) causing its polymerization, or, if a polyether is present in the reaction system, it may cause hydrogen abstraction. The very nature of the synthesis of Pluronic-PAA resulting in large amounts of polyether-radicals can cause instability of the copolymers in the presence of atmospheric oxygen. Degradation of polyethers in the presence of air at elevated temperatures has been described [Yang, Li; Heatley, Frank; Blease, Trevor G.; Thompson, Robert I. G. Eur. Polym. J. 1996, 32(5), 535-547] (This reference is explicitly included herein by reference.) and was shown to cause the loss of molecular weight. In PEO, significant structural changes were the formation of formate ester and hydroxy end-groups, the former predominating. In PPO, large amounts of primary hydroxy end-groups of the structure —OCH(CH$_3$)CH$_2$OH and secondary hydroxy end-groups of the structure —CH$_2$CH(CH$_3$)OH were formed, together with their formate and acetate esters. These structural changes were due to the decomposition of a peroxy species initally formed by substitution of a backbone hydrogen by a peroxy group.

Without being bound by any theory, the decomposition of the polyether segments of the Pluronic-PAA may involve the following general steps.

(7)

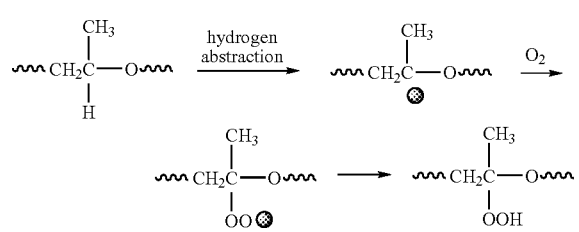

Step 1. Formation of Hydroperoxides

Considering the nature of the underlying free radical oxidation reaction (7), the amount of $O_2$ incorporation is not a simple function of aging time or temperature and is often dictated by trace impurities and catalysts. For instance, it may be generally affected by the presence of quinones and the like customarily added to the monomer for stability. The disappearance of the ether hydroperoxides via free radical decomposition leading to new radical initiation will create the remainder of the secondary degradation species

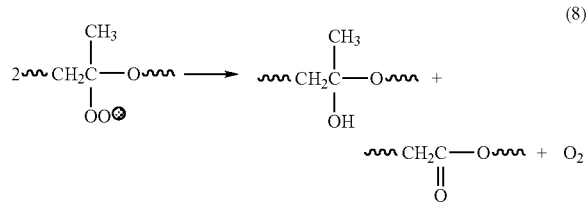

Step 2. Polyether Degradation-I (reaction 8). It can be postulated that in simple polyethers mechanism for the formation of ketones and alcohols is a bimolecular termination reaction of ether-peroxy radicals (eq 8). Tertiary peroxy radicals cannot undergo bimolecular termination via this mechanism; alternative multistep mechanisms still produce alcohols and ketones for tertiary radicals. If the termination shown in eq 8 were the only reaction, the concentration of ketones and alcohols would be equal. Chain scission via a cyclic peroxide intermediate can also be forwarded as a mechanism for the formation of ketones. Alkoxy radicals, formed from a homolysis reaction of the corresponding hydroperoxides, may also yield secondary alcohols (eq 9a) or aldehydes (eq 9b). A variety of different mechanisms for the production of alcohols and ketones can be suggested for the oxidation of polyethers.

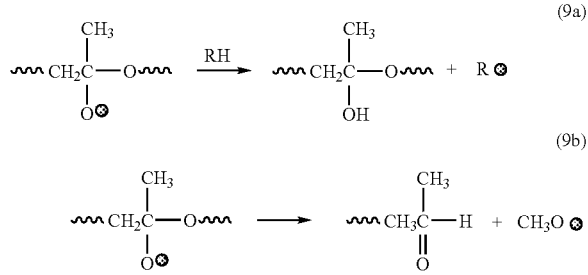

Step 3. Polyether Degradation-II

It must be noted that since degradation reactions discussed above lower the molecular weight of the polyether, they will dramatically affect the molecular weight of the Pluronic-PAA, because of the graft-comb structure of these copolymers. Since the gelation in aqueous solutions of Pluronic-PAA occurs via entropy-driven aggregation of PPO segments belonging to different Pluronic-PAA macromolecules, the lowering of the molecular weight will dramatically reduce or completely eliminate gelation in semidilute solutions of Pluronic-PAA.

In the present invention, we describe the method of stabilization of Pluronic-PAA solutions, in terms of preservation of their useful thermogelation ability, by minimizing the contact of the polymers with oxygen in the process of their synthesis.

The invention is illustrated by the following Examples.

EXAMPLE I

Synthesis of Pluronic-PAA Copolymers without Stabilization and the Polymer Instability Materials Pluronic F127 NF was obtained from BASF Corp. (Parsippany, N.J.) and used without further treatment. Acrylic acid (99%) was purchased from Aldrich Chemical Co. (Milwaukee, Wis.) and was vacuum-distilled prior to the use. Dodecane (98%) and ammonium persulfate (99+%) were obtained from Aldrich and used as received. Poly (vinylpyrrolidinone-co-1-hexadecene) (Ganex V-216) (dispersion stabilizer) was obtained from International Specialty Products (Wayne, N.J.) and used without further treatment. All other chemicals, gases and organic solvents of the highest purity available were obtained from commercial sources.

Synthesis

Synthesis was carried out on a laboratory scale in an adiabatic mode. Poly(ethylene oxide)-b-poly(propylene oxide)-b-(polyethylene oxide)-g-poly(acrylic acid) (CAS 4186810-81-1) was synthesized by dispersion/emulsion polymerization of acrylic acid as follows: Acrylic acid (40 g) in a 125-mL flask was partially neutralized by addition of 50 w/w % aqueous NaOH solution while stirring. The degree of neutralization of acrylic acid was 6 mol %. Upon redissolution of the formed precipitate, Pluronic (35 g) was charged into the flask and allowed to completely dissolve in acrylic acid under constant stirring. A 500-mL multinecked, thermostatted flanged glass reactor equipped with a mechanical stirrer, syringe sampler, thermometer, programmable heater bath, and a gas inlet/outlet was charged with 400 mL of 1 w/v % Ganex solution in dodecane and was deoxygenated for 2 h by nitrogen flow while stirring. Freshly prepared 300 mg/mL aqueous ammonium persulfate solution (4 mL) was added into the solution of Pluronic in acrylic acid under stirring. The resulting solution was deoxygenated by nitrogen flow for 0.5 h and introduced into the reactor under nitrogen purge. Then at t=0 the heating began and timing commenced. The reactor was heated up to 70° C. at 2° C./min under constant nitrogen flow and was kept at this temperature for 1 h under stirring. Then the reactor was allowed to equilibrate at 20° C., the nitrogen flow Was discontinued and the slurry of the resulting polymer was filtered off on air using Whatman filter paper (retention 10 μm). The polymer was repeatedly washed with excess hexane in separation funnels. The resultant white powder was dried in a rotor evaporator at 40° C. for 24 h and dissolved in DI water at room temperature under stirring and constant purging of the forming solution by gentle air bubbling. The pH was adjusted to 7.0 by 5M NaOH solution. The process of dissolution took about 4 days. The polymer resulting from the above synthetic procedure is termed "unstabilized" Pluronic-PAA.

Characterization Procedures

Rheological measurements of solutions of the Pluronic-PAA polymers were performed using a controlled stress Rheolyst Series AR1000 Rheometer (TA Instruments, New Castle, Del.) with a cone and plate geometry system (cone: diameter, 4 cm; angle, 2°, truncation, 57 μm). The systems were equipped with a solvent trap. Temperature control was provided by two Peltier plates.

The Pluronic-PAA solutions were placed in borosilicate glass bottles with vented closures and autoclaved for 30 minutes using a NAPCO 8000-DSE Benchtop Autoclave employing saturated steam under a pressure of 15 psi, chamber temperature of 121° C. and 100% relative humidity.

Results

The results of the rheological testing of the "unstabilized" Pluronic-PAA solution are presented in FIG. 1. As is seen, the gelation manifested in the increase of the complex viscosity ($\eta^*$) at certain temperature diminished. Without intending to be bound by a specific theory, this is thought to be the effect of the presence of hydroperoxides formed upon contact of the polymer particles (containing large concentration of radicals) with oxygen. Autoclaving resulted in chain scission and lowered the molecular weight of the polymer, which is reflected in the lack of viscosification.

In the case of the graft reverse thermal hydrogel as taught in FIGS. 1 and 2, we will define the term "transition range" to mean the temperature range within which the primary substantial increase in complex viscosity is occurring. In the case of FIG. 1, the transition range occurs from 27 degrees C. to about 40 degrees C. In the case of FIG. 2, it occurs from about 22 degrees C. to about 39 degrees C. In the case of FIG. 1, it can be more difficult to identify the upper end of the transition range because the complex viscosity of the material continues. However, there clearly is a break in the curve and a change in the slope of the viscosity-temperature curve. This break in the curve and change in the slope identifies the upper end of the viscosity-temperature curve. Since he transition range can be fairly broad, it is difficult to identify a single transition temperature. For the purposes of this work, we will define the term "transition temperature ($T_{transition}$)" to mean the midpoint of the transition range. Since in FIG. 1, the transition range is from about 27 degrees C. to about 40 degrees C., the transition temperature would be about 33.5 degrees C. Since in FIG. 2 the transition range is from about 22 degrees C. to about 39 degrees C., the transition temperature is about 30.5 degrees C.

In some cases, it has been observed for the graft reverse thermal hydrogels of the prior art that after autoclaving or after aging, in addition to the dimution or loss of complex viscosity in response to temperature increase, the transition range and transition temperature are shifted.

For the purposes of the calculation required by the claims, after the transition temperatures before and after autoclaving or aging are determined, an arbitrary temperature increment $\Delta T$ is selected and the complex viscosities of the solutions before and after autoclaving or aging are compared. For example, in FIG. 1, if one would select a value of $\Delta T$ of ten degrees, then the value of $T_{transition}+\Delta T$ would be 43.5 degrees C. The values of the complex viscosity shown on FIG. 1 are the following:

CHART 1

Retention of complex viscosity at the transition temperature for a graft reverse thermal hydrogel of the prior art

| Autoclave Cycles | Complex Viscosity Pa · sec | Retention |
|---|---|---|
| 0 | 9.41 | 100.0% |
| 1 | 7.84 | 83.3% |
| 2 | 3.78 | 40.2% |
| 3 | 1.27 | 13.5% |

The values of the complex viscosity in FIG. 1, FIG. 2, Chart 1 and Chart 2 are in P.a./sec. In contrast, if a similar comparison is made for FIG. 2, and one selected a value of $\Delta T$ of ten degrees, then $T_{transition}+\Delta T$ would be 40.5 degrees. A similar comparison of the values of the complex viscosity are shown below:

CHART 2

Retention of complex viscosity at the transition for a graft reverse thermal hydrogel embodying this invention

| Autoclave Cycles | Complex Viscosity Pa · sec | Retention |
|---|---|---|
| 0 | 16.23 | 100.0% |
| 1 | 15.42 | 95.0% |
| 2 | 15.41 | 94.9% |
| 3 | 15.88 | 97.9% |

In some cases, the solution becomes so degraded by autoclaving or by aging that no measurable change in viscosity is seen upon temperature increase and no transition range and transition temperature can be determined. In these cases, for the purposes of the calculation required by the claims, the same transition temperature should be used after autoclaving or aging as before autoclaving or aging

EXAMPLE II

Synthesis of Pluronic-PAA Copolymers Stabilized by Minimizing Exposure to Air and by Removal of Unstable Species by Lyophilization Materials All materials were obtained as in Example 1.

Synthesis

Acrylic acid (40 g) in a 125-mL flask was partially neutralized by addition of 50 w/w % aqueous NaOH solution while stirring. The degree of neutralization of acrylic acid was 6 mol %. Upon redissolution of the formed precipitate, Pluronic (35 g) was charged into the flask and allowed to completely dissolve in acrylic acid under constant stirring. A glass reactor as in Example 1 was charged with 400 mL of 0.2 w/v % Ganex solution in dodecane and was deoxygenated overnight by nitrogen flow while stirring. Freshly prepared 300 mg/mL aqueous ammonium persulfate solution (2 mL) was added into the solution of Pluronic in acrylic acid under stirring. The resulting solution was deoxygenated by nitrogen flow for 0.5 h and introduced into the reactor under nitrogen purge. Then at t=0 the heating began and timing commenced. The reactor was heated up to 70° C. at 2° C./min under constant nitrogen flow and was kept at this temperature for 2 h under stirring. Then the reactor was allowed to equilibrate at 20° C., the nitrogen flow was discontinued and the slurry was transferred to the separation funnel with excess hexane under nitrogen blanket. The polymer powder was then dried under vacuum (1 mTorr) at 40° C. overnight and the dry powder was kept at −70° C. The Pluronic-PAA powder was then dissolved in deaerated 0.1 M NaOH solution at 4° C. while bubbling nitrogen through the solution. The resulting 10 w/v % solution was snap-frozen in liquid nitrogen and lyophilized for 48 h at 1-5 mTorr using a VirTis Freezemobile freeze dryer. The resulting fluffy powder was quickly dissolved in DI water at 2 w/v % and pH was adjusted to 7.0. The solutions were tested rheologically as described in Example 1.

Results

The results of the Theological testing of the "stabilized" Pluronic-PAA solution are presented in FIG. 2. The observed gelation was not appreciably affected by 3 cycles of autoclaving.

EXAMPLE III

Graft Reverse Thermal Hydrogel which is Stabilized to Degradation by Aging

The graft reverse thermal hydrogel of Example II is allowed to age for one year at 25 degrees C. Measurement of the complex viscosity at a temperature $T_{transition}+\Delta T$ where $\Delta T$ is between 0 and 20 degrees C. shows that the complex viscosity is 90% of greater of the complex viscosity measured prior to aging.

We claim:

1. A process for the manufacture of stable graft reverse thermal hydrogel in which the graft reverse thermal hydrogel comprises a stable free radical graft copolymer of polyacrylic acid or neutralized polyacrylic acid and polyoxyalkylene polymer comprising:
    a) Providing the raw materials required for the polymerization
    b) Deaerating the reactant solution prior to polymerization
    c) Conducting a free radical polymerization with air and oxygen excluded
    d) Working up the reaction products with air and oxygen excluded to isolate the stable free radical graft copolymer
    wherein air and oxygen are excluded during synthesis from the beginning of the step of free radical polymerization until the step of working up the reaction products to produce the stable free radical graft copolymer is completed.

2. The process of claim 1 for the manufacture of stable graft reverse thermal hydrogel in which the graft reverse thermal hydrogel comprises a stable free radical graft copolymer of polyacrylic acid or partially neutralized or fully neutralized polyacrylic acid and polyoxyalkylene polymer further comprising:
    a) Providing the raw materials required for the polymerization
    b) Deaerating the reactant solution prior to polymerization
    c) Conducting a free radical polymerization with air and oxygen excluded
    d) Working up the reaction products with air and oxygen excluded
    e) Dissolving the reaction products into aqueous solution with air and oxygen excluded
    f) Snap freezing the aqueous solution with air and oxygen excluded
    g) Lyophilizing the aqueous solution with air and oxygen excluded
    wherein air and oxygen are excluded during synthesis from the beginning of the step of free radical polymerization until the steps of snap freezing and lyophilizing the aqueous solution are completed.

3. A stable free radical graft copolymer obtained by the process of claim 2.

4. A solution comprising the solution of the stable free radical graft copolymer of claim 3 in water.

5. The process of claim 1 for the manufacture of stable graft reverse thermal hydrogel in which the graft reverse thermal hydrogel comprises a stable free radical graft copolymer of polyacrylic acid or neutralized polyacrylic acid and polyoxyalkylene polymer further comprising:
    a) Providing the raw materials required for the polymerization
    b) Deaerating the reactant solution prior to polymerization
    c) Conducting a free radical polymerization with air and oxygen excluded
    d) Working up the reaction products with air and oxygen excluded
    e) Dissolving the reaction products into aqueous solution with air and oxygen excluded
    f) Removing the water from the aqueous solution with air and oxygen excluded to isolate the stable free radical graft copolymer
    wherein air and oxygen are excluded during synthesis from the beginning of the step of free radical polymerization until the step of removing the water from the aqueous solution is completed.

6. A stable free radical graft copolymer obtained by the process of claim 5.

7. A solution comprising the solution the stable free radical graft copolymer of claim 6 in water.

8. A stable free radical graft copolymer obtained by the process of claim 1.

9. A solution comprising the solution of the stable free radical graft copolymer of claim 8 in water.

10. The solution of claim 9 which comprises stable graft free radical copolymer in the concentration range between 0.0001% and 20%.

11. The solution of claim 10 which comprises stable graft free radical copolymer in the concentration range between 0.0001% and 10%.

12. The solution of claim 11 which comprises stable graft free radical copolymer in the concentration range between 0.0001% and 5%.

13. The solution of claim 12 which comprises stable graft free radical copolymer in the concentration range between 0.0001% and 2%.

14. The solution of claim 13 which comprises stable graft free radical copolymer in the concentration range between 0.0001% and 1%.

15. A free radical graft copolymer of polyacrylic acid or partially neutralized or fully neutralized polyacrylic acid and polyoxyakylene polymer of chemical structure poly(ethylene oxide)-b-poly(propylene oxide)-b-poly(ethylene oxide)-g-poly(acrylic acid) which when dissolved in water will produce a solution comprising a graft reverse thermal hydrogel of chemical structure poly(ethylene oxide)-b-poly(propylene oxide)-b-poly(ethylene oxide)-g-poly(acrylic acid) wherein the improvement comprises that the solution is stable so that, when measured at a temperature $T_{transition}+\Delta T$ where $\Delta T$ is between 0 and 20 degrees C., displays a complex viscosity after one cycle of autoclaving for 30 minutes at a temperature of 121 degrees C. which is not less than 80% of its complex viscosity prior to autoclaving when measured at $T_{transition}+\Delta T$ where $\Delta T$ has the same value as after autoclaving.

16. The copolymer of claim 15 wherein the improvement further comprises that the solution is stable so that, when measured at a temperature $T_{transition}+\Delta T$ where $\Delta T$ is between 0 and 20 degrees C., displays a complex viscosity after one cycle of autoclaving for 30 minutes at a temperature of 121 degrees C. which is not less than 90% of its complex viscosity prior to autoclaving when measured at $T_{transition}+\Delta T$ where $\Delta T$ has the same value as after autoclaving.

17. The copolymer of claim 16 wherein the improvement further comprises that the solution is stable so that, when measured at a temperature $T_{transition}+\Delta T$ where $\Delta T$ is between 0 and 20 degrees C., displays a complex viscosity after one cycle of autoclaving for 30 minutes at a temperature of 121 degrees C. which is not less than 95% of its complex viscosity prior to autoclaving when measured at $T_{transition}+\Delta T$ where $\Delta T$ has the same value as after autoclaving.

18. The copolymer of claim 15 wherein the improvement further comprises that the solution is stable is stable so that, when measured at a temperature $T_{transition}+\Delta T$ where $\Delta T$ is between 0 and 20 degrees C., displays a complex viscosity after two cycles of autoclaving for 30 minutes at a temperature of 121 degrees C. which is not less than 80% of its complex viscosity prior to autoclaving when measured at $T_{transition}+\Delta T$ where $\Delta T$ has the same value as after autoclaving.

19. The copolymer of claim 18 wherein the improvement further comprises that the solution is stable so that, when measured at a temperature $T_{transition}+\Delta T$ where $\Delta T$ is between 0 and 20 degrees C., displays a complex viscosity after two cycles of autoclaving for 30 minutes at a temperature of 121 degrees C. which is not less than 90% of its complex viscosity prior to autoclaving when measured at $T_{transition}+\Delta T$ where $\Delta T$ has the same value as after autoclaving.

20. The copolymer of claim 19 wherein the improvement further comprises that the solution is stable so that, when measured at a temperature $T_{transition}+\Delta T$ where $\Delta T$ is between 0 and 20 degrees C., displays a complex viscosity after two cycles of autoclaving for 30 minutes at a temperature of 121 degrees C. which is not less than 95% of its complex viscosity prior to autoclaving when measured at $T_{transition}+\Delta T$ where $\Delta T$ has the same value as after autoclaving.

21. A solution comprising the copolymer of claim 15 in water.

22. The free radical graft copolymer of claim 15 in which the polyoxyalkylene polymer further does not comprise a polyoxyalkylene polymer in which at least one end is terminated by a functionality selected from the group consisting of acrylate, polymerized acrylate, amino, acryloyl, polymerized acryloyl, thiol and polymerized thiol.

23. A free radical graft copolymer of polyacrylic acid or partially neutralized or fully neutralized polyacrylic acid and polyoxyakylene polymer polymer of chemical structure poly(ethylene oxide)-b-poly(propylene oxide)-b-poly(ethylene oxide)-g-poly(acrylic acid) which when dissolved in water will produce a solution comprising a graft reverse thermal hydrogel of chemical structure poly(ethylene oxide)-b-poly(propylene oxide)-b-poly(ethylene oxide)-g-poly(acrylic acid) wherein the improvement comprises that the solution is stable so that, when measured at a temperature $T_{transition}+\Delta T$ where $\Delta T$ is between 0 and 20 degrees C., displays a complex viscosity after being allowed to age for one year which is not less than 80% of its complex viscosity prior to aging when measured at $T_{transition}+\Delta T$ where $\Delta T$ has the same value as after aging.

24. A solution comprising the solution of the copolymer of claim 23 in water.

25. A solution comprising a free radical graft reverse thermal hydrogel of chemical structure poly(ethylene oxide)-b-poly(propylene oxide)-b-poly(ethylene oxide)-g-poly(acrylic acid) comprising the free radical graft copolymer of polyacrylic acid or partially neutralized or fully neutralized polyacrylic acid and polyalkylene polymer of chemical structure poly(ethylene oxide)-b-poly(propylene oxide)-b-poly(ethylene oxide)-g-poly(acrylic acid) of claim 23.

26. A free radical graft copolymer of polyacrylic acid or partially neutralized or fully neutralized polyacrylic acid and polyoxyakylene polymer of chemical structure poly(ethylene oxide)-b-poly(propylene oxide)-b-poly(ethylene oxide)-g-poly(acrylic acid) which does not comprise sufficient groups selected from the group consisting of peroxides, oxides, hydroperoxides and other oxygen reaction products bonded to the central polymer backbones or the grafts which arise from the reaction of air or oxygen with free radicals on the central polymer backbones or grafts to cause instability so that when the free radical branched graft copolymer is dissolved in water it will produce a free graft reverse thermal hydrogel of chemical structure poly(ethylene oxide)-b-poly(propylene oxide)-b-poly(ethylene oxide)-g-poly(acrylic acid) which produces a solution which when measured at a temperature $T_{transition}+\Delta T$ where $\Delta T$ is between 0 and 20 degrees C., displays a complex viscosity after one cycle of autoclaving for 30 minutes at a temperature of 121 degrees C. which is not less than 80% of its complex viscosity prior to autoclaving when measured at $T_{transition}+\Delta T$ where $\Delta T$ has the same value as after autoclaving.

27. A solution comprising a free radical graft reverse thermal hydrogel of chemical structure poly(ethylene oxide)-b-poly(propylene oxide)-b-poly(ethylene oxide)-g-poly(acrylic acid) comprising a free radical graft copolymer of polyacrylic acid or partially neutralized or fully neutralized polyacrylic acid and polyalkylene polymer of chemical structure poly(ethylene oxide)-b-poly(propylene oxide)-b-poly(ethylene oxide)-g-poly(acrylic acid) wherein the improvement comprises that the solution is stable so that, when measured at a temperature $T_{transition}+\Delta T$ where $\Delta T$ is between 0 and 20 degrees C., displays a complex viscosity after one cycle of autoclaving for 30 minutes at a temperature of 121 degrees C. which is not less than 80% of its complex viscosity prior to autoclaving when measured at $T_{transition}+\Delta T$ where $\Delta T$ has the same value as after autoclaving.

* * * * *